United States Patent
Sarathy et al.

(10) Patent No.: US 11,175,035 B2
(45) Date of Patent: Nov. 16, 2021

(54) BURNERS FOR CONVERSION OF METHANE TO OLEFINS, AROMATICS, AND NANOPARTICLES

(71) Applicant: King Abdullah University of Science and Technology, Thuwal (SA)

(72) Inventors: Mani Sarathy, Thuwal (SA); Robert Dibble, Thuwal (SA); William Roberts, Thuwal (SA)

(73) Assignee: KING ABDULLAH UNIVERSITY OF SCIENCE AND TECHNOLOGY, Thuwal (SA)

(*) Notice: Subject to any disclaimer, the term of this patent is extended or adjusted under 35 U.S.C. 154(b) by 153 days.

(21) Appl. No.: 16/340,566

(22) PCT Filed: Oct. 10, 2017

(86) PCT No.: PCT/IB2017/056264
§ 371 (c)(1),
(2) Date: Apr. 9, 2019

(87) PCT Pub. No.: WO2018/069837
PCT Pub. Date: Apr. 19, 2018

(65) Prior Publication Data
US 2020/0049346 A1 Feb. 13, 2020

Related U.S. Application Data

(60) Provisional application No. 62/406,089, filed on Oct. 10, 2016.

(51) Int. Cl.
*F23D 99/00* (2010.01)
*B01J 15/00* (2006.01)
(Continued)

(52) U.S. Cl.
CPC .......... *F23D 91/02* (2015.07); *B01J 15/005* (2013.01); *B01J 19/0013* (2013.01);
(Continued)

(58) Field of Classification Search
CPC .... B01J 15/005; B01J 19/0013; B01J 19/249; B01J 2219/00157; C01P 2004/64;
(Continued)

(56) References Cited

U.S. PATENT DOCUMENTS 3,079,236 A * 2/1963 Heller .................... F23D 14/00
423/456
4,026,670 A * 5/1977 Henderson ............... C09C 1/50
422/150
(Continued)

FOREIGN PATENT DOCUMENTS

EP 2255872 A2 12/2010
FR 2109083 A5 * 5/1972 .............. C09C 1/50
(Continued)

OTHER PUBLICATIONS

Notification of Transmittal of the International Search Report and the Written Opinion of the International Searching Authority, or the Declaration for PCT/IB2017/056264 dated Feb. 1, 2018.

*Primary Examiner* — Jorge A Pereiro
*Assistant Examiner* — Logan P Jones
(74) *Attorney, Agent, or Firm* — Billion & Armitage

(57) ABSTRACT

Embodiments of the present disclosure describe burner (10) configurations used in an industrial process to convert methane to olefins, aromatics, and nanoparticles/nanomaterials. Both a vitiated coflow burner and piloted turbulent burner with inhomogeneous inlets are disclosed.

7 Claims, 5 Drawing Sheets

(51) Int. Cl.
*B01J 19/00* (2006.01)
*B01J 19/24* (2006.01)
*C07C 2/84* (2006.01)
*C09C 1/30* (2006.01)
*C09C 1/36* (2006.01)
*C09C 3/06* (2006.01)
*F23C 6/04* (2006.01)
*F23C 13/00* (2006.01)
*F23D 14/02* (2006.01)
*F23D 14/26* (2006.01)
*F23D 14/32* (2006.01)
*F23D 14/58* (2006.01)
*F23C 5/06* (2006.01)

(52) U.S. Cl.
CPC ............... *B01J 19/249* (2013.01); *C07C 2/84* (2013.01); *C09C 1/3054* (2013.01); *C09C 1/3661* (2013.01); *C09C 3/063* (2013.01); *F23C 6/047* (2013.01); *F23C 13/00* (2013.01); *F23D 14/02* (2013.01); *F23D 14/26* (2013.01); *F23D 14/32* (2013.01); *F23D 14/58* (2013.01); *B01J 2219/00157* (2013.01); *C01P 2004/64* (2013.01); *C01P 2004/82* (2013.01); *F23C 2900/03002* (2013.01); *F23D 2203/102* (2013.01); *F23D 2900/21007* (2013.01)

(58) Field of Classification Search
CPC ..... C01P 2004/82; C07C 2/84; C09C 1/3054; C09C 1/3661; C09C 3/063; F23C 13/00; F23C 2900/03002; F23C 2900/9901; F23C 5/06; F23C 6/047; F23D 14/02; F23D 14/26; F23D 14/32; F23D 14/58; F23D 2203/102; F23D 2900/21007; F23D 91/02

See application file for complete search history.

(56) References Cited

U.S. PATENT DOCUMENTS

| | | | | |
|---|---|---|---|---|
| 4,179,494 | A * | 12/1979 | Rothbuhr | C09C 1/50 423/456 |
| 4,643,667 | A * | 2/1987 | Fleming | F23D 14/16 431/328 |
| 5,729,967 | A | 3/1998 | Joos et al. | |
| 5,876,684 | A * | 3/1999 | Withers | B82Y 40/00 423/445 B |
| 6,979,433 | B1 * | 12/2005 | Saito | B82Y 30/00 423/447.1 |
| 7,279,137 | B2 * | 10/2007 | Alford | C01B 32/15 422/129 |
| 7,442,227 | B2 * | 10/2008 | Rosen | B22F 1/0018 75/255 |
| 8,069,671 | B2 | 12/2011 | Alstom | |
| 9,388,042 | B2 * | 7/2016 | Tse | C01B 3/363 |
| 2003/0143151 | A1 * | 7/2003 | Diener | B82Y 30/00 423/447.3 |
| 2004/0179989 | A1 * | 9/2004 | Height | C01B 32/154 423/447.3 |
| 2007/0264172 | A1 * | 11/2007 | Mosimann | F23D 14/84 422/150 |
| 2008/0314202 | A1 * | 12/2008 | Park | C22C 1/08 75/363 |
| 2009/0126604 | A1 * | 5/2009 | Akhtar | B82Y 30/00 106/438 |
| 2013/0273430 | A1 * | 10/2013 | Axelbaum | H01M 4/525 429/224 |
| 2014/0056766 | A1 | 2/2014 | Bedard et al. | |

FOREIGN PATENT DOCUMENTS

| | | | | |
|---|---|---|---|---|
| GB | | 670863 A * | 4/1952 | ............... C09C 1/50 |
| JP | | 06159633 A * | 6/1994 | |

* cited by examiner

BURNERS FOR CONVERSION OF METHANE TO OLEFINS, AROMATICS, AND NANOPARTICLES

BACKGROUND

Current methods of methane conversion typically require integration of several complex catalytic reaction technologies. Efficient conversion of methane, the dominant component of natural and shale gases, into key chemical feedstock and liquid fuels remains a significant challenge in chemistry and chemical engineering. Industrial processes for methane-derived higher hydrocarbons (e.g., olefin, aromatics) have typically been based on indirect methane conversion integrating several catalytic reaction technologies.

Light olefins (e.g., ethylene and propylene) are important basic petrochemicals used to produce plastics, fibers and other chemicals. Most light olefins are produced by steam cracking. Steam cracking involves combustion and pyrolysis processes. Traditional industrial reactor processes (e.g., Hoescht process) decouple the combustion and pyrolysis processes within two or more reactor components.

SUMMARY

In general, embodiments of the present disclosure describe reactor designs for oxy-methane combustion and pyrolysis. The reactor embodiments of the present disclosure further describe an integrated burner configuration for combining both a methane/oxygen combustion process and subsequent pyrolysis of methane to form olefins (ethylene, acetylene, etc.), aromatics (benzene, naphthalene, etc.) and nanoparticles (carbon black, carbon nanotubes, etc.).

One embodiment of the present disclosure includes a vitiated co-flow burner. The use of catalysts is also possible with the vitiated coflow burner. Another embodiment of the present disclosure includes a piloted turbulent burner with inhomogeneous inlets. In both embodiments, seed particles or the production of nanoparticles/nanomaterials may also be utilized. If such precursors are delivered in the coflow stream, then the produced nanoparticle/nanomaterials undergo further reactions to produce functionalized nanoparticles.

Embodiments of the present disclosure further describe methods of controlling secondary reactions of a burner of combustion products using injected methane comprising providing a jet flame in coaxial flow of hot combustion products from a premised vitiated coflow of gas passing through a porous plate, providing a tube positioner to translate a central tube tip and controlling the tube positioner to vary the offset heights of the central tube in a dynamic manner based on chemical inputs to yield different secondary reactions of combustion.

Embodiments of the present disclosure describe two burner configurations adaptable for industrial processes to convert methane to olefins, aromatics, and nanoparticles/nanomaterials. The details of one or more examples are set forth in the description below. Other features, objects, and advantages will be apparent from the description and from the claims.

BRIEF DESCRIPTION OF DRAWINGS

This written disclosure describes illustrative embodiments that are non-limiting and non-exhaustive. In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

Reference is made to illustrative embodiments that are depicted in the figures, in which.

DETAILED DESCRIPTION

The present disclosure relates to burner configurations used in an industrial processes to convert methane and related compounds to olefins, aromatics, and nanoparticles/nanomaterials. One embodiment of the present disclosure describes a vitiated coflow burner. Another embodiment of the present disclosure describes a piloted turbulent burner with inhomogeneous inlets.

Figure 1:
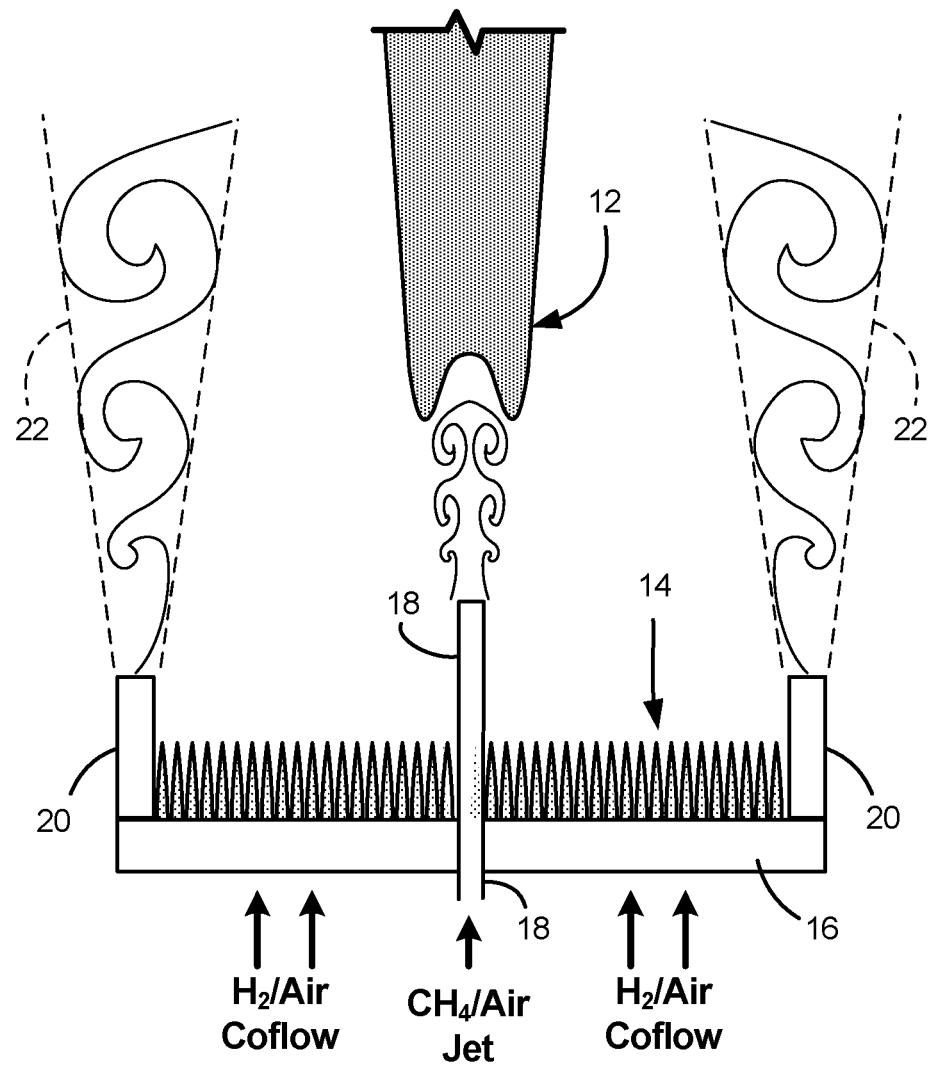
FIG. 1 illustrates a vitiated coflow burner configuration in accordance with one or more embodiments of the present disclosure.

The first burner configuration is a vitiated co-flow burner 10 as shown in FIG. 1. The burner design includes a jet flame 12 in coaxial flow of hot combustion products from a premixed flame (vitiated coflow) 14. Coflow gas (CH4/O2) passes through a porous plate 16 prior to combustion with gas (CH4) from central tube 18. Porous plate 16 may be generally circular centered about tube 18. Coflow gas originates from a remote vessel (not shown) with gas pressure and gas flow rate being controlled. A generally cylindrical exit collar 20 contains the jet flame 12 and coflow flames 14 and establishes a shear boundary 22 surrounding jet flame 12.

In general terms, coflow burner 10 defines two concentric tubes with an annulus that supplies premixed methane and oxygen via porous plate 16, and a blunt-tipped central tube 18 that delivers methane. Central tube 18 can be translated vertically such that a methane jet is injected into the "hot" coflow combustion gases at various positions relative to porous plate 16. The offset-height of tube 18, and thus position of the methane injection, determines the temperature at which reactions occur, and thereby determines the yield and selectivity to various products. The methane/oxygen mixture fraction (equivalence ratio) in the premixed co-flow can vary from lean to rich conditions, in order to vary the downstream temperature field, as well as the secondary reactions of combustion products with methane injected from central tube 18.

Porous plate 16 may include a porous metal, perforated plate or various metal screens. The material used for the porous plate can be selected based on material properties (e.g., thermal conductivity, metal temperature, reactivity, machinability, etc).

Figure 2:
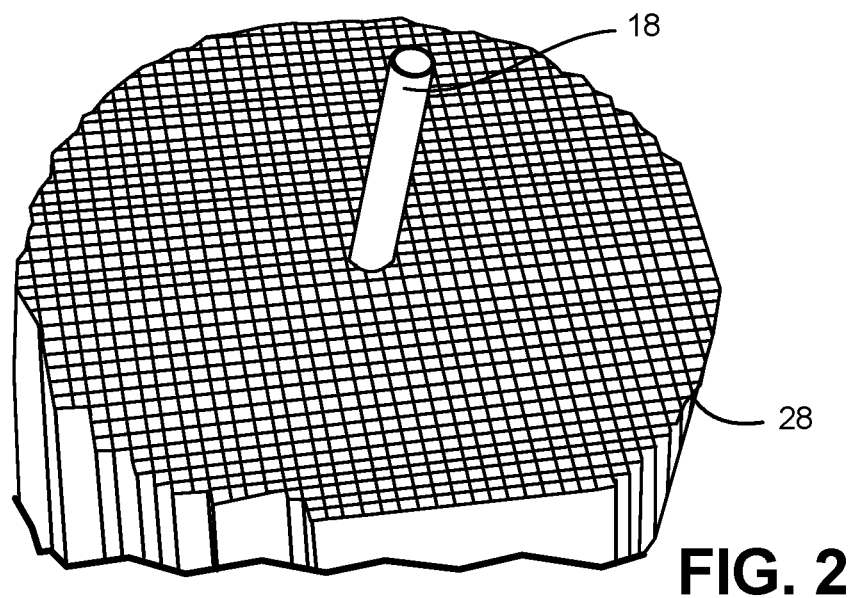
FIG. 2 illustrates vitiated coflow burner configuration having a monolithic catalyst in accordance with one or more embodiments of the present disclosure.

Catalysts can be used in the vitiated coflow burner. FIG. 2 shows an alternative embodiment of a vitiated coflow burner having a catalytic monolith 28. In this embodiment, the coflow stream passes through ceramic monolith 28 coated by catalytic materials instead of porous plate 16. A straight-channel monolith 28 is shown in FIG. 2. The catalysts partially convert the methane/oxygen to desirable products, and thereby facilitates secondary reactions with the central methane jet. Seed particles or the production of nanoparticles/nanomaterials may also be utilized, either in the central methane jet or the coflow streams. If such precursors are delivered in the coflow stream, then the produced nanoparticle/nanomaterials undergo further reactions with the central methane jet, thereby producing functionalized nanoparticles (e.g., carbon coated $TiO_2$, carbon coated $SiO_2$, etc.).

Figure 3:
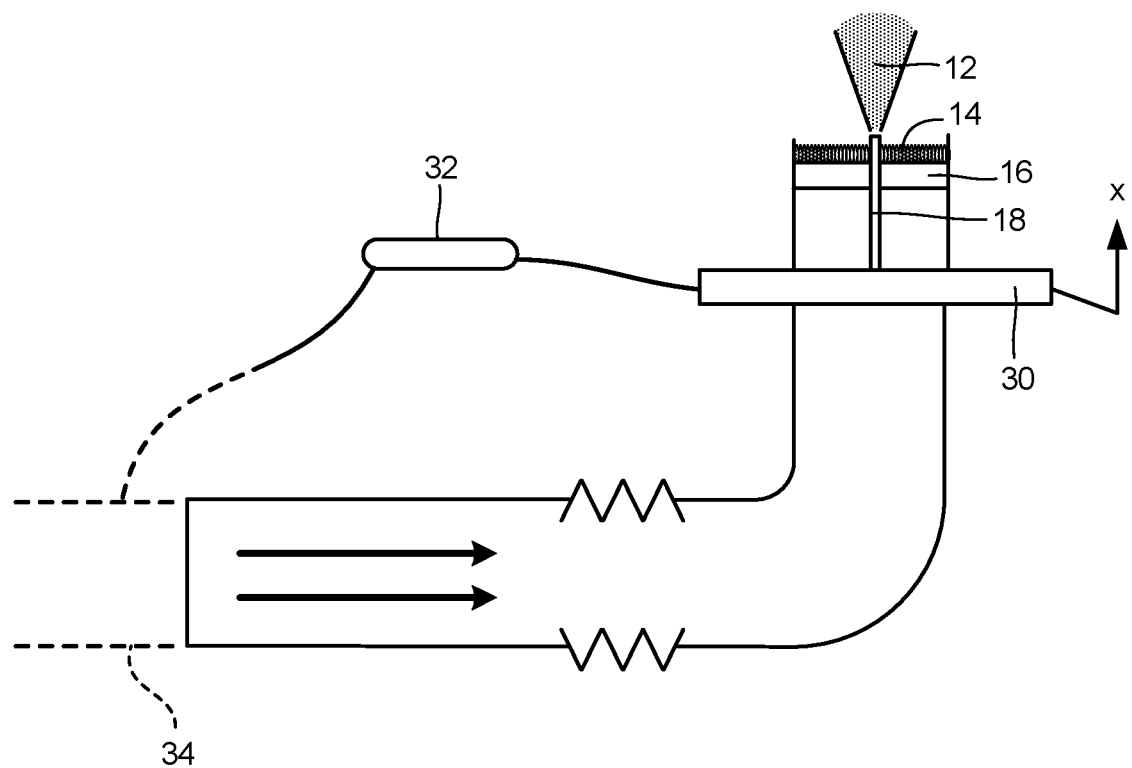
FIG. 3 illustrates a schematic of an embodiment of the present disclosure including a burner wherein the tip height of the central tube is controlled.

FIG. 3 illustrates a schematic of an embodiment of the present disclosure including a burner design wherein the tip height of the central tube 18 relative to porous plate 16 is mechanically or electromechanically controlled via tip positioner 30. A variety of linkages, actuators, etc., could be utilized within tip positioner 30 to translate central tube 18 relative to porous plate 16. A controller 32 can be utilized to control tip positioner 30 to adjust the position of the central tube 18 in a dynamic manner based on chemical inputs and/or desired outputs of the burner. The controller 32 could also adjust the coflow composition, e.g., from lean to rich condition in order to vary the downstream temperature field and secondary reactions of combustion products, via a flow control system 34.

The flow control system 34 includes flow supply, control and data acquisition systems. For example, methane is fed through the inner tube 18 while air/gas is fed through the outer tube. More specifically, the method includes the step of feeding the methane from a fuel supply source through a metering valve and flow meter to the central tube 18 of the burner. As described, central tube 18 is held by a positioner 30 in the flame region of the diffusion flame.

Figure 4:
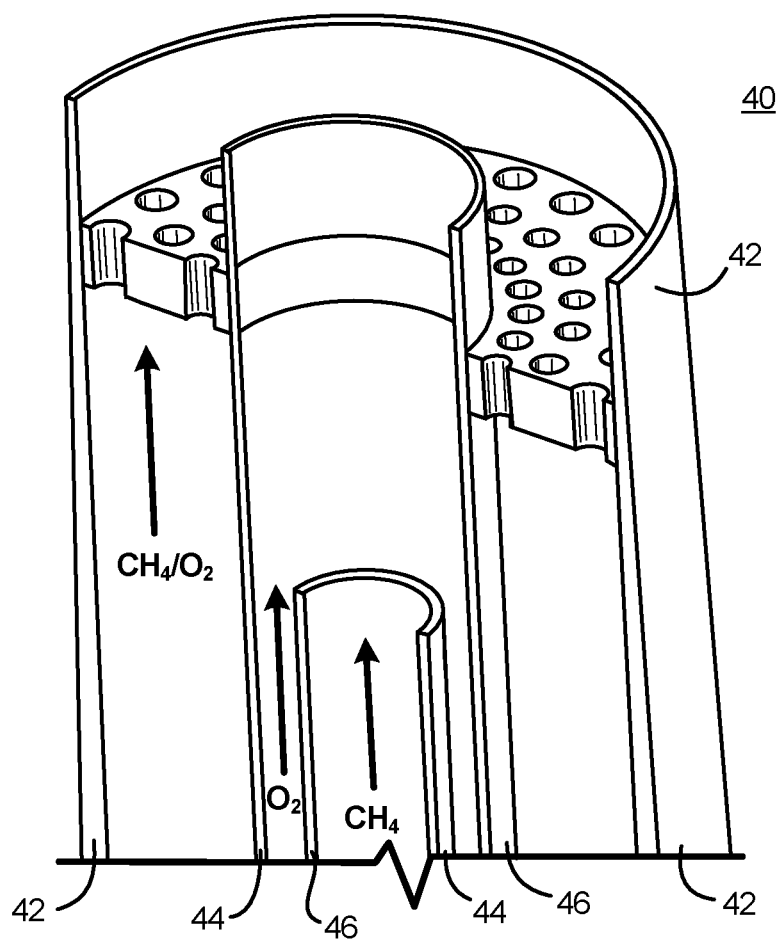
FIG. 4 illustrates a piloted turbulent flame burner with inhomogeneous inlets in accordance with one or more embodiments of the present disclosure.

FIG. 4 illustrates a second burner configuration including a piloted turbulent burner 40 with inhomogeneous inlets. Burner 40 defines three concentric tubes 42, 44, 46 defining gas conduits for the burner. The outermost tube 42 delivers a mixture of methane and oxygen, which is used to ignite a premixed flame. This flame supplies the heat needed for pyrolysis of methane to various desired products. The innermost tube 44 delivers methane while the intermediate tube 46 delivers oxygen. The innermost tube 44 can be translated vertically (axially within intermediate tube 46) such that a methane jet is injected into the oxygen, and various levels of premixing can be achieved before the mixture reacts in the main high temperature zone (i.e., the premixed methane/oxygen flame region). The position of the methane injection and the oxygen flow rate determine the yield and selectivity to various products. The methane/oxygen mixture fraction (equivalence ratio) in the premixed co-flow jets can vary from lean to rich conditions, in order to vary the downstream temperature field, as well as the secondary reactions of combustion products with the methane/oxygen mixture from the inner tubes. Seeding particles or the production of nanoparticles/nanomaterials may also be utilized, either in the innermost tube 44 or the outermost tube 42. If such precursors are delivered in the coflow stream, then the produced nanoparticle/nanomaterials undergo further reactions with the central methane jet, thereby producing functionalized nanoparticles (e.g., carbon coated $TiO_2$, carbon coated $SiO_2$, etc.).

Figure 5:
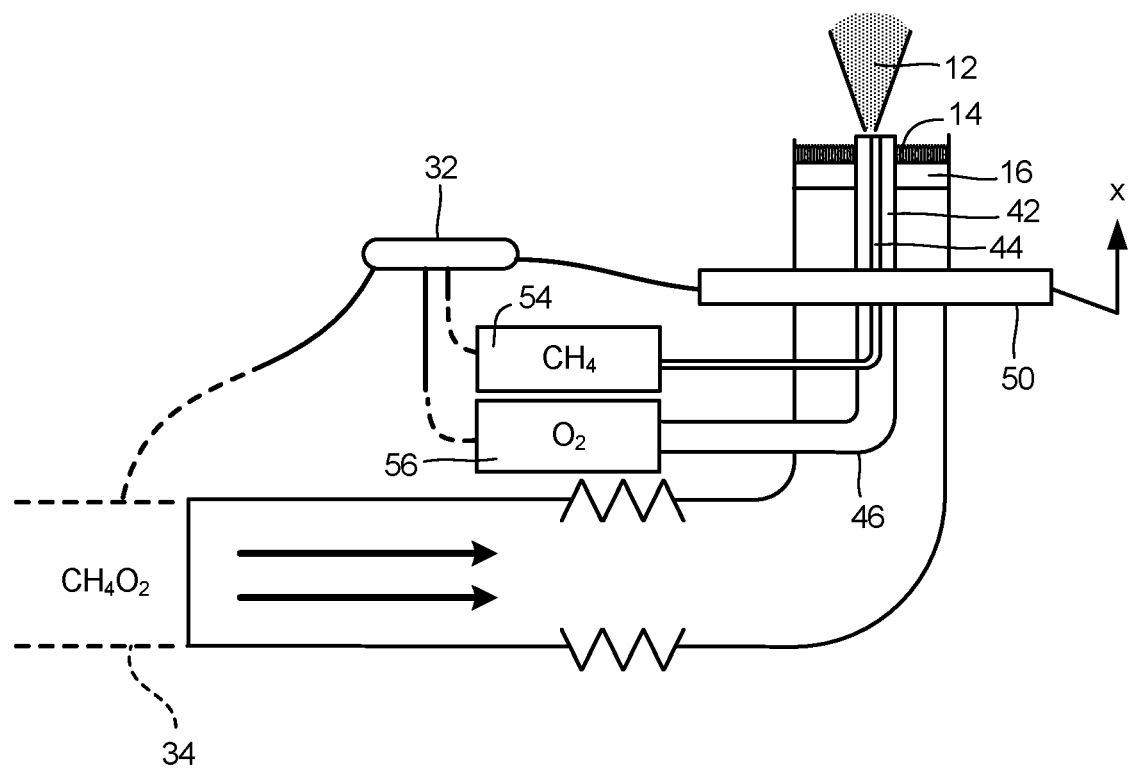
FIG. 5 illustrates a schematic of an embodiment of the present disclosure including a piloted turbulent flame burner of FIG. 4.

FIG. 5 illustrates a schematic of an embodiment of the present disclosure including a piloted turbulent burner design wherein the axial position of the innermost supply tube 44 within intermediate tube 46 is mechanically or electromechanically controlled via tube positioner 50. A variety of linkages, actuators, etc., could be utilized within tube positioner 50 to translate the innermost tube 44 relative to intermediate tube 46. For example, a controller 32 can be utilized to control tube positioner 50 to adjust the position of the innermost tube 44 in a dynamic manner based on chemical inputs and/or desired outputs of the burner. The controller 32 could also adjust the composition of the premixed coflow (CH4 and O2), e.g., from lean to rich condition in order to vary the downstream temperature field and secondary reactions of combustion products, via a flow control system 34. The flow control system 34 includes flow supply, control and data acquisition systems. Controller 32 can be utilized to control the flow within innermost tube 44 via flow control system 54 and the flow within intermediate tube 46 via flow control system 56.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto Various examples have been described. These and other examples are within the scope of the following claims.

What is claimed is:

1. A method of controlling secondary reactions of a burner of combustion products using injected methane, the method comprising:

establishing a premixed flame from a gas mixture passing through a porous plate or catalytic monolith, with said premixed flame forming a high temperature zone for pyrolysis and being established by a piloted turbulent burner with inhomogeneous inlets and defining three concentric tubes, wherein an outermost tube of the piloted turbulent burner supplies said gas mixture;

providing a tube positioner to translate an innermost one of the three concentric tubes to different positions relative to an intermediate tube, wherein the innermost tube supplies a first gas and the intermediate tube supplies a second gas; and controlling the tube positioner to vary the position of the innermost tube in a dynamic manner based on chemical inputs, with said controlling resulting in different levels of mixing of the first gas and the second gas prior to entering the high temperature zone.

2. The method of claim 1, wherein the innermost tube is a blunt-tipped tube and the gas exiting the innermost tube is methane.

3. The method of claim 1, wherein oxygen is supplied via the intermediate tube and a combination of methane and oxygen is supplied by the outermost tube.

4. The method of claim 1, wherein the position of the innermost tube is controlled to facilitate both a methane/oxygen combustion process and subsequent pyrolysis of methane to form olefins, aromatics or nanoparticles.

5. The method of claim 1, wherein gas flowing through an outermost tube passes through a porous plate or catalytic monolith to ignite the premixed flame.

6. A burner for converting injected methane to olefins, aromatics and nanoparticles/nanomaterials, comprising:

a perforated plate through which a coflow gas passes, with a coflow flame established above the plate;

a central tube passing through the plate and having a tip through which methane exits, with a jet flame established above the central tube;

an exit ring surrounding the plate, with said exit ring establishing a shear boundary of combustion products;

a tube positioner for varying an offset height of the tube tip relative to the plate; and a controller for adjusting the offset height of the tube tip based on material inputs or desired output yield, wherein the central tube is one of three concentric tubes for gas delivery, including an innermost tube delivering methane, an intermediate tube delivering oxygen, and an outermost tube delivering a mixture of methane and oxygen, with the mixture of methane and oxygen from the outermost tube passing through the perforated plate, and with said innermost tube being translatable within the intermediate tube to vary the position of the tube tip relative to the perforated plate.

7. The burner of claim 6, wherein the perforated plate includes a porous plate or catalytic monolith.

* * * * *